United States Patent [19]

McDonald

[11] Patent Number: 5,766,182
[45] Date of Patent: Jun. 16, 1998

[54] MULTIPLE FOLDING AND HANDLING OF OPTICAL LENS UNIT FOR PLACEMENT IN THE EYE

[75] Inventor: Henry H. McDonald, 525 E. Cordova St., #100, Pasadena, Calif. 91101

[73] Assignees: Henry H. McDonald; William W. Haefliger, both of Pasadena, Calif.; a part interest

[21] Appl. No.: 779,755

[22] Filed: Jan. 7, 1997

Related U.S. Application Data

[63] Continuation-in-part of Ser. No. 680,683, Jul. 17, 1996, Pat. No. 5,711,317.

[51] Int. Cl.⁶ .................................. A61F 9/00; A61F 2/16
[52] U.S. Cl. .................................. 606/107; 623/6
[58] Field of Search .................................. 623/6; 606/107

[56] References Cited

U.S. PATENT DOCUMENTS

| | | | |
|---|---|---|---|
| 4,304,012 | 12/1981 | Richard | 623/6 |
| 4,573,998 | 3/1986 | Mazzocco | 623/6 |
| 4,747,404 | 5/1988 | Jampel et al. | 623/6 X |
| 4,769,035 | 9/1988 | Kelman | 623/6 |
| 4,785,810 | 11/1988 | Baccala et al. | 623/6 X |
| 4,813,957 | 3/1989 | McDonald | 606/107 |
| 4,959,070 | 9/1990 | McDonald | 606/107 |
| 5,203,790 | 4/1993 | McDonald | 623/6 |
| 5,217,464 | 6/1993 | McDonald | 606/107 |

FOREIGN PATENT DOCUMENTS

| | | | |
|---|---|---|---|
| 436232 | 7/1991 | European Pat. Off. | 606/107 |

*Primary Examiner*—Mary Beth Jones
*Attorney, Agent, or Firm*—William W. Haefliger

[57] ABSTRACT

The method of compacting an artificial lens for implantation into the eye that includes imparting to the lens an M shape having two laterally spaced legs interconnected by a U-shaped portion; and laterally deflecting the legs toward and into compacting relation with the U-shaped portion.

20 Claims, 7 Drawing Sheets

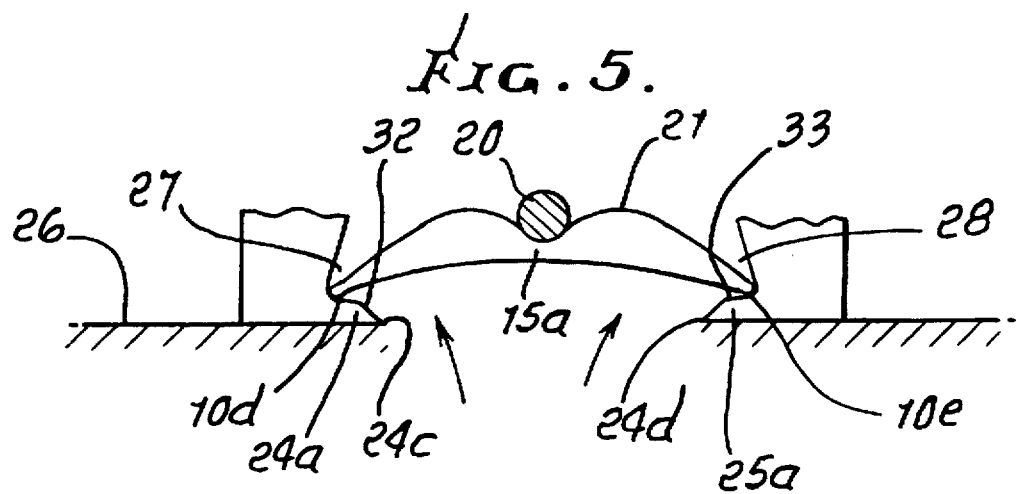
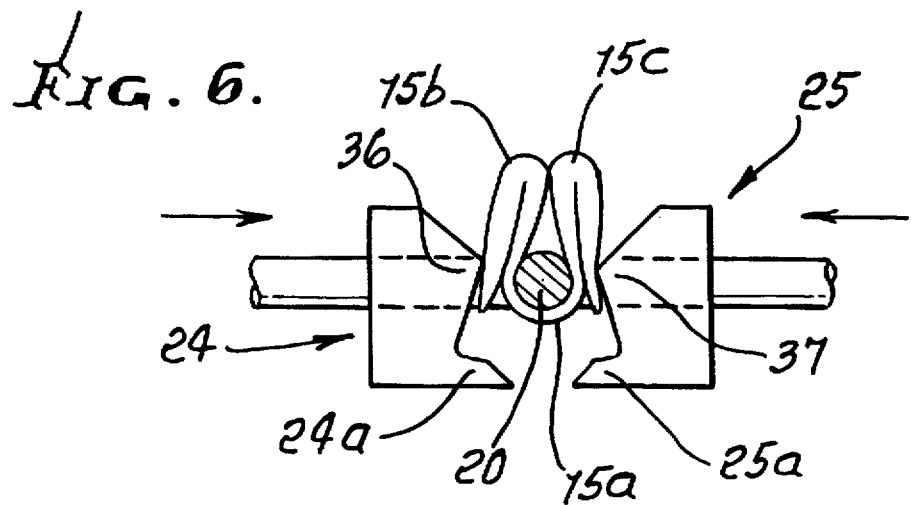
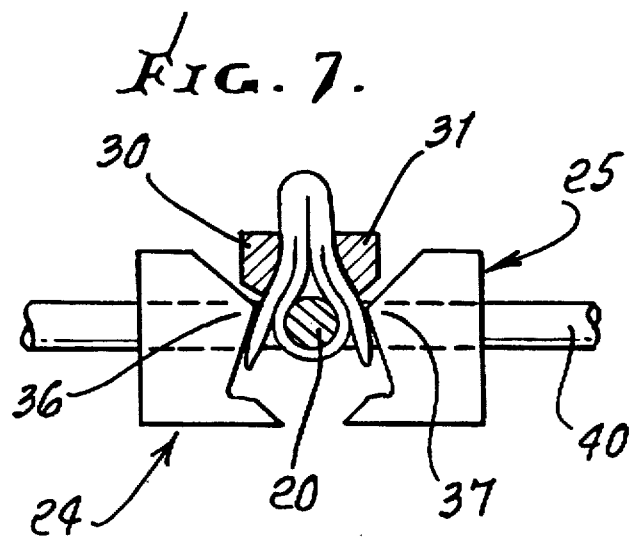

Fig. 9.
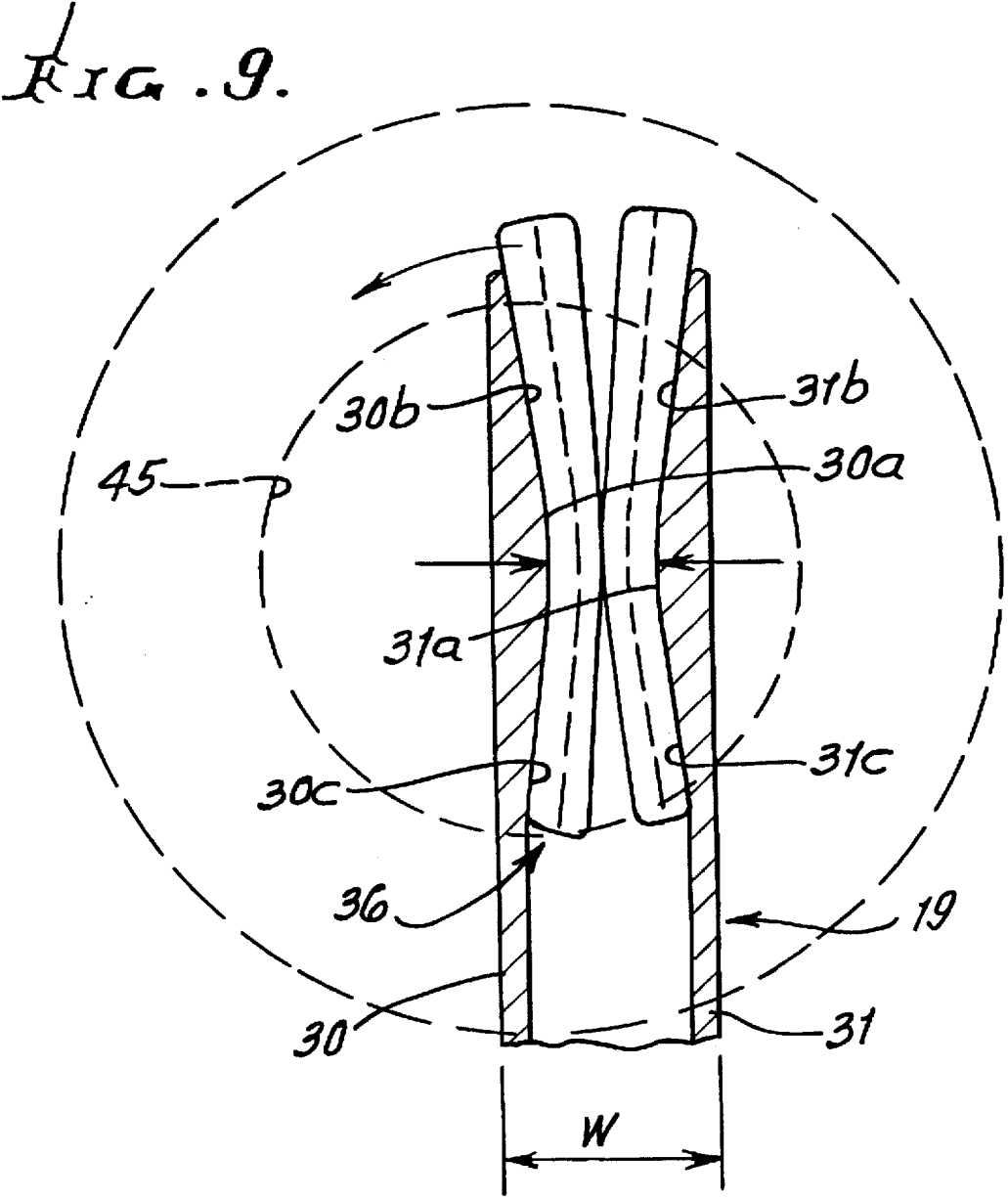
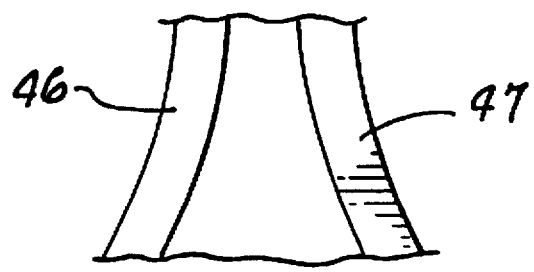

MULTIPLE FOLDING AND HANDLING OF OPTICAL LENS UNIT FOR PLACEMENT IN THE EYE

BACKGROUND OF THE INVENTION

This application is a continuation-in-part of prior U.S. application Ser. No. 08/680,683 filed Jul. 17, 1996, now U.S. Pat. No. 5,711,317.

This invention relates generally to insertion of an artificial lens unit into the eye; and more particularly to creation of a multi-folded lens unit, and grasping of same, for insertion into a very small wound opening in the eye, whereby very rapid lens replacement surgery can be achieved, with minimum disruption of the eye.

There is constant need for improvements in eye surgery, particularly in lens implant surgery, to achieve faster and more efficient lens insertion and positioning, as well as reduced size eye wound openings in the interests of faster healing. There is particular need in these regards, for implants in intraocular lens implant surgery.

Prior techniques are believed not to incorporate or suggest the unusual improvements in method and apparatus which are the subject of the present invention.

SUMMARY OF THE INVENTION

It is a major object of the invention to provide method and apparatus meeting the above needs, and providing for faster, more efficient, and less disruptive lens implant surgery.

Basically, the present method includes the steps:

a) imparting to the lens an M shape having two laterally spaced legs interconnected by a U-shaped portion, and b) laterally deflecting the legs toward and into compacting relation with the U-shaped portion.

Additional objects include:

c) folding the lens unit to form at least three folds, d) grasping the folded unit to hold it in folded state, and then inserting the folded unit into the eye through an opening formed in the eye.

Such imparting typically includes folding the lens at loci proximate the interconnection of the legs with the U-shaped portion, and also at a locus proximate a crest defined by the U-shaped portion. Also, such deflecting of the legs typically includes displacing them toward a crest defined by the U-shaped portion.

Another object includes providing a bar, and folding the lens under the bar to produce the U-shaped portion. Tool structure, including two deflectors, is typically provided for displacement adjacent the lens legs, to deflect the legs toward one another. Also, the U-shaped lens portion has two segments compacted toward one another by the displaced lens legs, in response to such deflection. The bar may be withdrawn away from the compacted lens, to allow the lens to be supported by the deflectors, and ultimately by the arms of a lens inserter. The inserted arms embrace the lens legs after compacting deflection of the legs.

The tool bar may be slidably supported by the tool structure that includes the deflectors, to allow relative withdrawing of the bar away from the U-shaped lens portion, whereby the lens may be supported by the deflectors.

Another object is to provide for controlled grasping of the lens edges by such tool structure, in order to bow the lens upwardly under the bar.

As will be seen, the lens unit is thereby typically folded to form an M-shape, as in cross section, in order to pass through a very small wound in the eye wall. In this regard, the lens unit may have haptics so as to be initially elongated, and the multiple folds are formed to extend in the lens elongation direction, i.e., toward both haptics.

It is another object to provide a folding tool having lens-folding elements that extend in elongated, parallel directions, and may be narrow, to deflect a very small artificial lens.

Yet another object is to provide the lens unit in folded state to have elongation between folded haptics at opposite ends of the unit, and the grasping pinches the folded unit to greater extent at a location medially of the unit than at locations proximate its ends.

An additional object is to provide for release of lens unit grasping after the lens unit has been inserted endwise into the eye, whereby completed unfolding of the unit folds at its opposite ends precedes completed unfolding of the folds at the medial location. In this regard, the lens unit grasping elements, such as arms, are provided to have lens unit pinching surfaces located to pinch the folded unit to greater extent at a location medially of the unit than at locations proximate its opposite ends. Such surfaces of the grasping tool typically have convex extents presented oppositely, toward opposite side folds of the folded unit.

Release of such a medially pinched lens thereby proceeds gradually, instead of explosively, with the medially pinched portion of the lens unit completing its unfolding after completion of unfolding of lens unit opposite ends, thereby minimizing potential impact damage to the eye structure.

A yet further object is to insert the multi-folded lens into the eye zone between the iris and cornea of the eye, via a very small eye wound opening, so that unfolding will not damage the natural lens or its surface. Subsequently, and after completion of lens unit unfolding, as from M shape, the reshaped lens unit is manipulated, a portion at a time, into the intraocular zone between the iris and the natural lens, for ultimate, safe placement adjacent the natural lens surface.

Additional objects include provision of apparatus or tools to accomplish multiple folding of a very small plastic lens unit, and its positioning in the eye, for safe unfolding, as referred to. As will appear, such apparatus typically includes elements to form at least three folds, and an M-shaped folded lens may be formed.

These and other objects and advantages of the invention, as well as the details of an illustrative embodiment, will be more fully understood from the following specification and drawings, in which:

DRAWING DESCRIPTION

FIG. 5 is a fragmentary view showing lens edge grabbing;

FIG. 6 is a view like FIG. 5 but showing deflecting elements approaching the outermost folds of the lens;

FIG. 7 is a view like FIG. 6 but showing the lens folds pushed more closely together by lens-grasping elements, to be used as lens inserters, into the eye;

3

Figure 8:
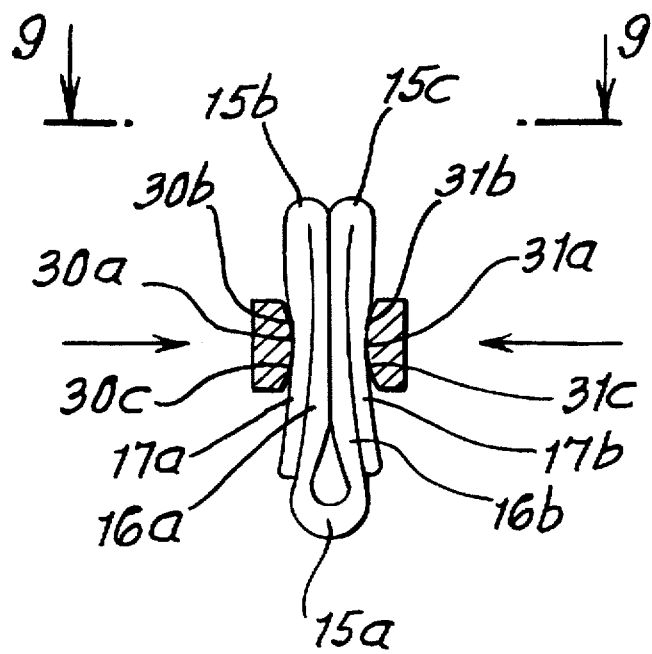
FIG. 8 is a view like FIG. 7 but showing the lens folds variably pinched together by the grasping elements, in preparation for insertion through a very small eye wound opening into the eye.
Figure 8A:
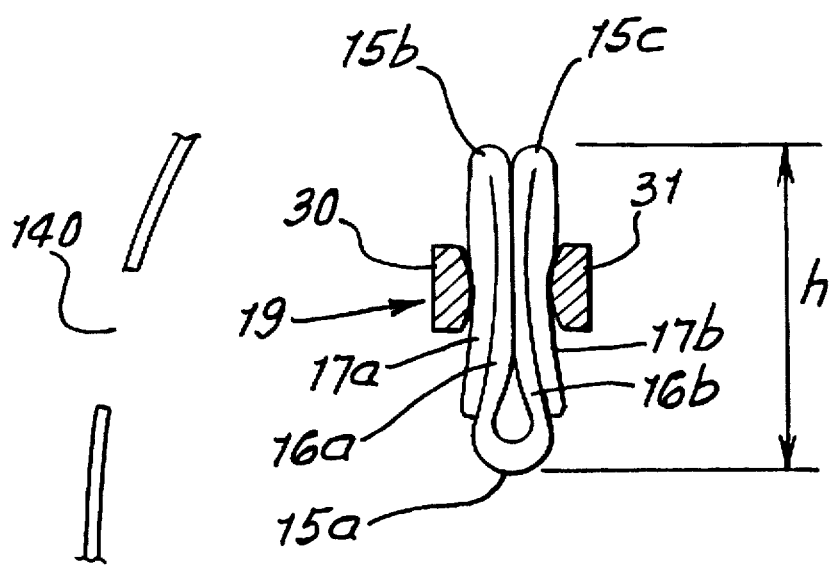
FIG. 8a is similar to FIG. 8.
Figure 10:
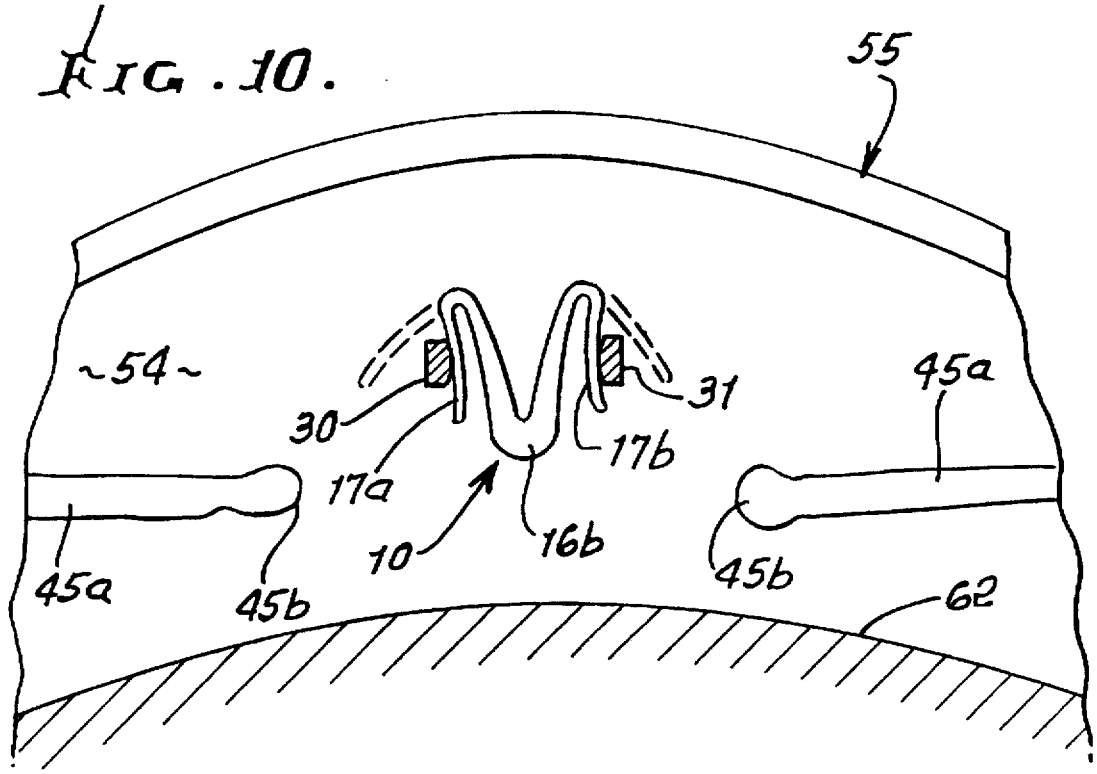
Figure 11:
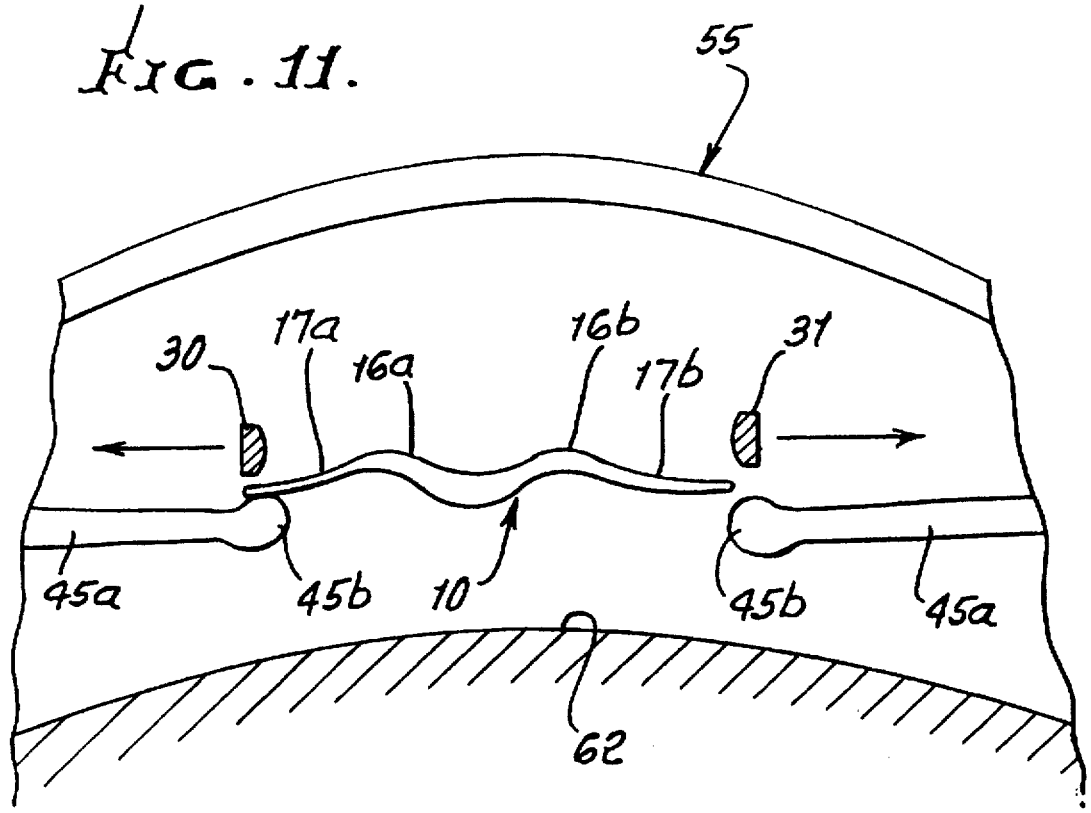
Figure 12:
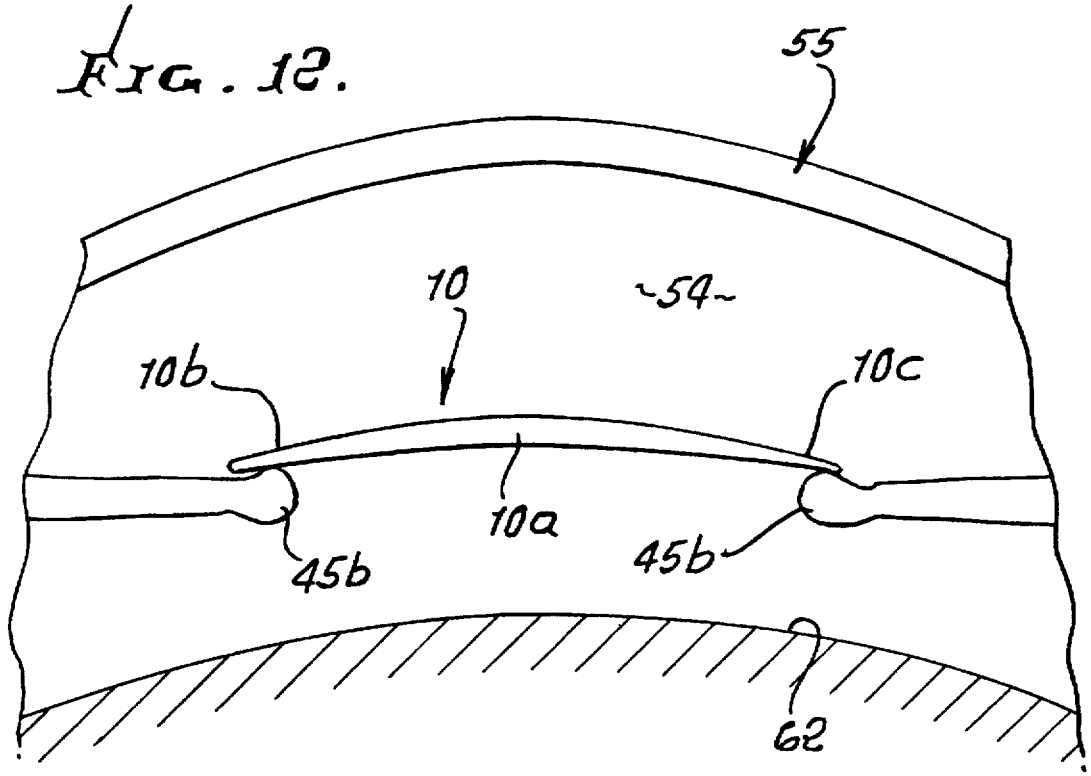
Figure 13:
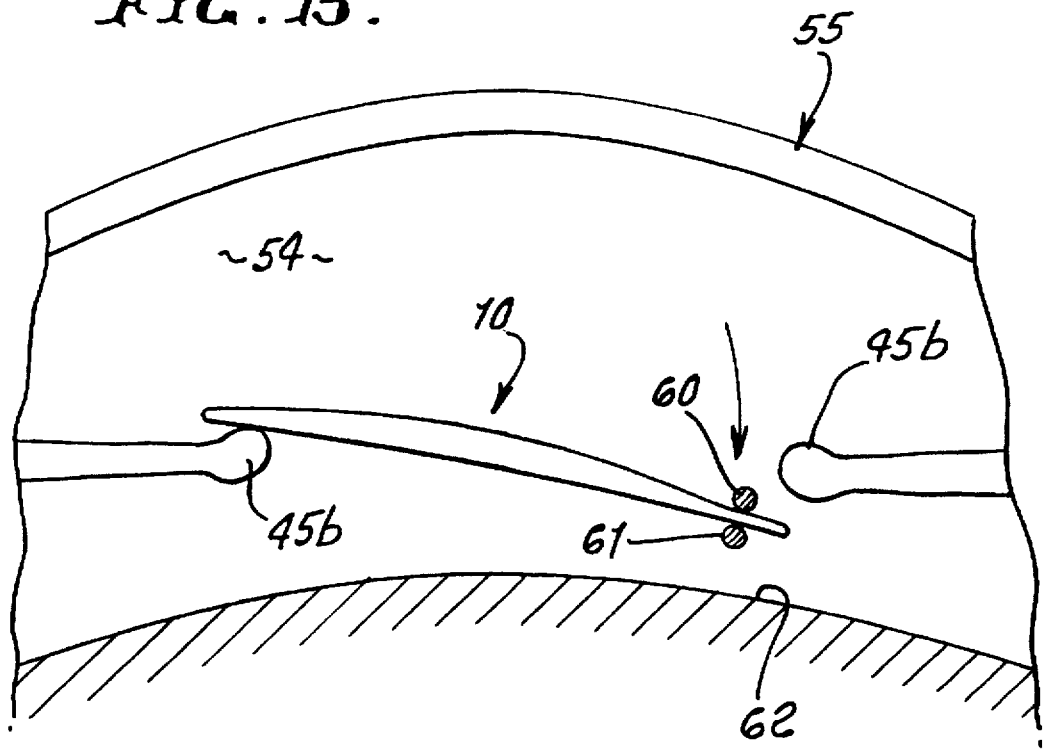
Figure 14:
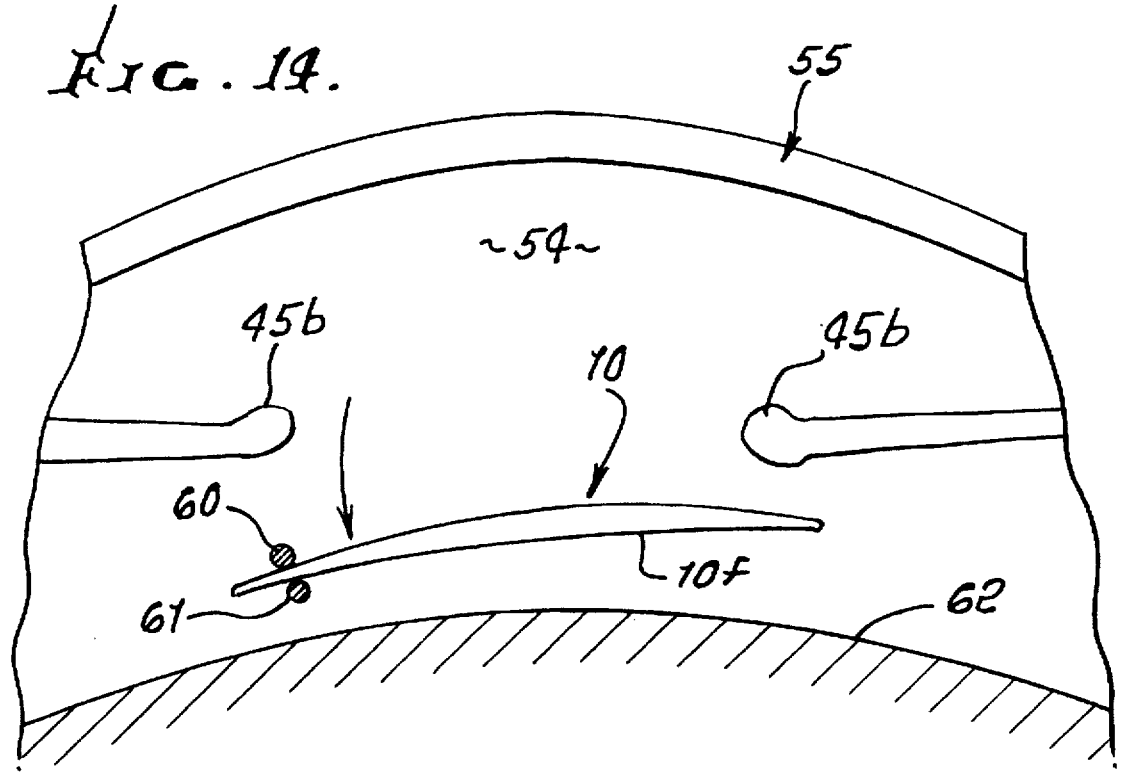
Figure 15:
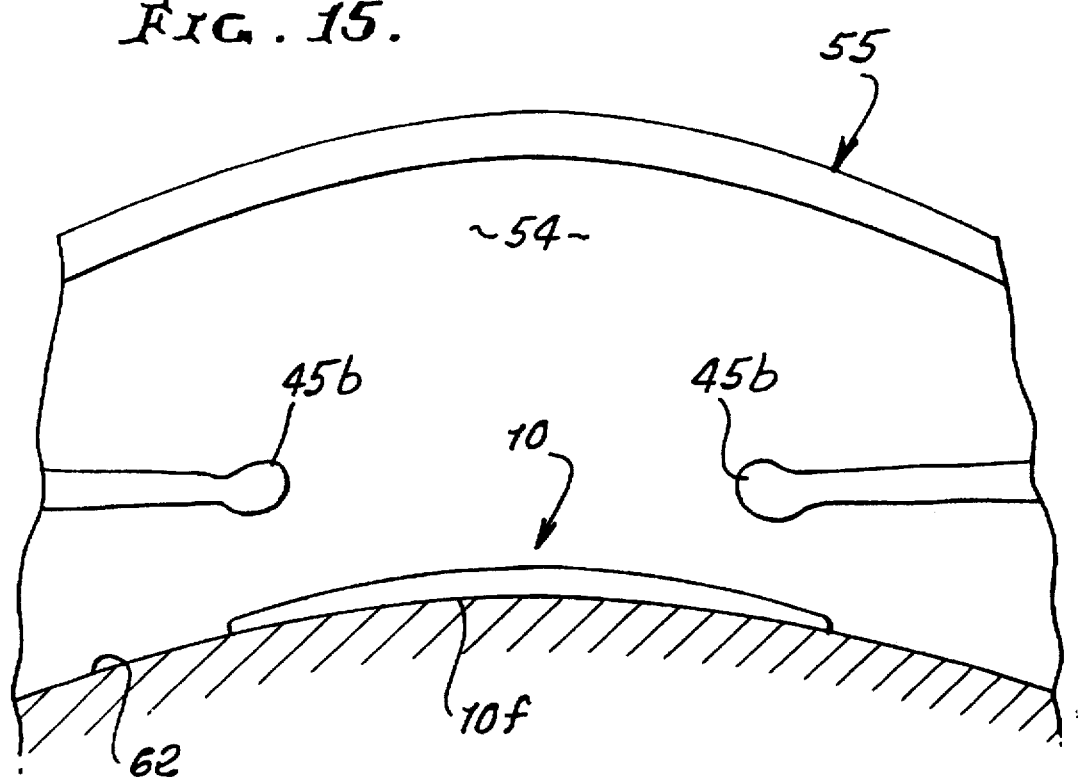

FIG. 9 is an enlarged view taken on lines 9—9 of FIG. 8 showing the multi-folded lens inserted into the eye between the iris and the cornea;

FIGS. 10–12 are elevations showing progressive release of the folded lens in the eye, in response to separation of the grasping elements;

FIG. 13 is a view showing haptic or lens edge portion, being displaced below the iris and toward the natural lens of the eye;

FIG. 14 is a view like FIG. 13 showing another haptic, or lens edge portion, being displaced below the iris and toward the natural lens of the eye, the entire lens then positioned below the iris; and FIG. 15 is a view like FIG. 14 showing the artificial lens positioned directly adjacent the surface of the natural lens.

DETAILED DESCRIPTION

Figure 3:
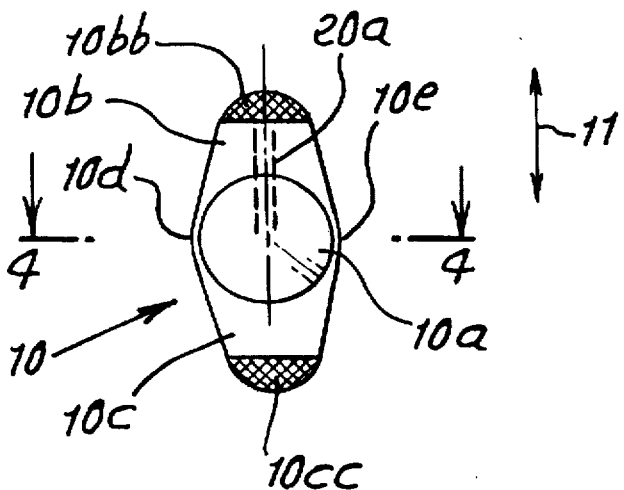
FIG. 3 is a plan view of a lens or lens about to be folded.
Figure 4:
FIG. 4 is a section taken on lines 4—4 of FIG. 3.

In FIGS. 3 and 4, a plastic lens unit 10 has a central, generally circular, relatively thicker, lens zone 10a, and two tabular haptics 10b and 10c. If desired, the haptics may be filamentary. The unit is elongated in direction 11, and its thickness decreases as shown at the haptics. The lens unit may typically be sized and constructed for insertion into the inter-ocular zone of the eye, between the cornea and natural lens, to be allowed to controllably unfold, as in the sub-zone between the iris and the cornea, i.e., spaced from the natural lens for maximum protection of the natural lens, during unfolding. Examples of lens material are collamer and silicone resin. Means is provided herein for folding the lens unit at multiple locations, to form at least three folds, such as accordian folds, to compact the lens for insertion into the eye via a very small slit in the eye wall.

In FIG. 8, the parallel fold bend locations are seen at 15a–15c, in alignment with the fold forming parallel elements, to be described. The folded lens includes a U-shaped portion having segments 16a and 16b extending upwardly from 15a, and legs 17a and 17b extending downwardly from 15b and 15c, and deflected toward segments 16a and 16b, to compact the lens for insertion into the eye. Insertion bar elements or tongs of an inserter 19 appear at 30 and 31, to grasp the lens via legs 17a and 17b. See for example U.S. patent application Ser. No. 08/680,683, incorporated herein by reference.

Accordingly, the method of the invention, for compacting an artificial lens for implanting into the eye, includes the steps:

a) imparting to the lens an M shape having two laterally spaced legs interconnected by a U-shaped portion, and b) laterally deflecting the legs toward and into compacting relation with the U-shaped portion. Such imparting includes folding the lens at loci proximate the interconnection of the legs with the U-shaped portion, and also at a locus proximate a crest defined by the U-shaped portion.

In order to fold the lens, as described, a bar 20 may be used, as shown in FIGS. 5 and 6. Circular bar 20 is supported to extend in the direction of the folding, i.e., directly above the initial fold, locus at 15a. Note that the lens bulges upwardly, i.e., is convex upwardly at that location; and a dip 21 is formed by the bar in the resilient bulge. The locus of bar placement appears at 20a in FIG. 3, to extend over the haptics 10b and 10c. If desired, it is advantageous to provide open-work mesh regions 10bb and 10cc at outer edges of the haptics, to locate at the inner edge of the lens capsule, and to enhance anchoring of the lens by reception of adhesions or eye tissue in the mesh regions.

4

Structure is provided, as in FIGS. 5 and 6, to "grasp" the edges 10d and 10e of the lens unit, to locate them for pushing them toward one another, to produce the fold at 15a. See for example the lens "grabbers" 24 and 25 having projections, such as lifters 24a and 25a, with edges 24c and 24d that reach under the lens edges on a support surface 26 to lift and locate such lens edges in angled recesses 27 and 28 defined by 24 and 25. Cam surfaces 32 and 33 on the projections act to cam the lens edges upwardly and into the recesses, as the projections 24 and 25 move relatively toward one another. This is important for handling soft, gelatinous lenses, such as callamer material.

The grabbers 24 and 25 also include deflectors 36 and 37 that taper toward the lens legs 17a and 17b, to push them toward the lens segments 16a and 16b, as in FIG. 7, and particularly after bar 20 is pulled out or removed endwise. Legs 17a and 17b are shown in side-by-side stacked, compacting relation to segments 17a and 17b, which, together with fold 15a, form a lens U-shaped portion. The lens-grasping elements 30 and 31 are also applied, as in FIGS. 7 and 8, to further collapse the compacted lens, for insertion into the eye.

Figure 1:
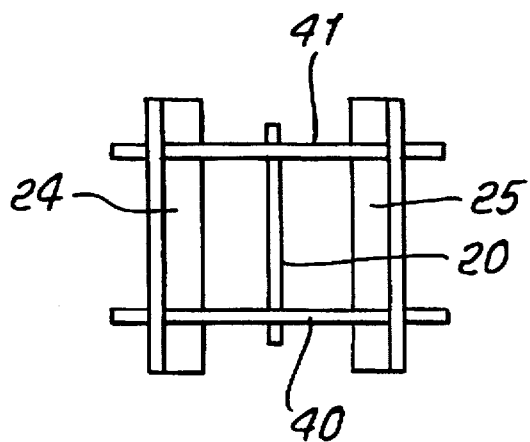
FIG. 1 is a plan view of a lens-compacting tool structure.
Figure 2:
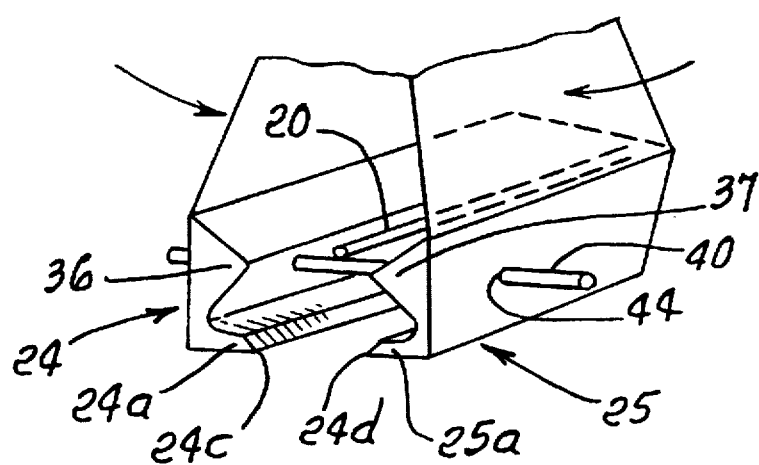
FIG. 2 is a perspective view of the FIG. 1 structure.
Figure 2A:
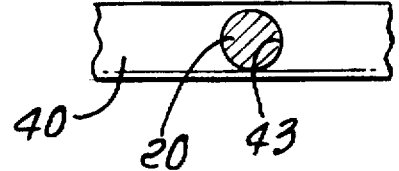
FIG. 2a is an enlarged fragmentary view of bars in said structure.

FIGS. 1 and 2 show how bar 20 is supported by two cross bars 40 and 41. The latter are supported by structure 24 and 25. H-shaped bars 20, 40 and 41 are removed by removing bar 20 from openings 43 in bars 40 and 41, and by endwise removing bars 40 and 41 from openings 44 in 24 and 25.

Opposite end portions of the folded lens unit are not pinched together, but may flare apart slightly as shown in FIG. 8. Note that the facing sides of the tongs, as at 30b and 31b are spaced apart to greater extent than at 30a and 31a, this relationship also appearing at 30c and 31c, to produce such flaring.

FIGS. 8 and 9 show the folded lens unit occupying minimum width "we", and minimum height "h", for entry through a minimum height and width wound at 140 in the wall of the eye.

That wound may, for example, have a slit length of about 0.5 to 2 mm or larger. The smallness of the wound results in minimum disruption of the eye, and promotes faster healing. The insertion techniques, as disclosed herein, also promote faster surgery.

Note in FIG. 9 that the folded unit may be inserted in offset relation to the center of the eye, as defined by the iris opening 45. The insertion tool handles or arms 46 and 47, attached to the lens-grasping units 30 and 31, may be maneuvered to position the folded lens in centered relation to the iris.

FIG. 10 shows the positioning of the folded lens unit in the chamber 54 between the iris 45a and the cornea 55. As the grasping elements 30 and 31 are moved apart, the opposite end portions of the lens outer folds, as represented at 17a and 17b, spread apart to greater extent than the mid portions of the inner folds, whereby an explosive unfolding of the lens is prevented.

Thus, as seen in FIG. 11, by the time that the folds 16a and 16b are allowed to spread apart, as by retraction of 30 and 31, the outer folds have almost completely unfolded toward the iris portion 45b.

FIG. 12 shows the completely unfolded lens unit, positioned just above the iris.

FIG. 13 shows use of a tool having arms 60 and 61 maneuvering one end of the lens unit into the space below the iris and toward natural lens surface 62; and FIG. 14 shows use of that tool to maneuver the opposite end of the lens unit below the iris, in position for application to the natural lens surface.

FIG. 15 shows the unfolded lens with its lower concave side 10f very closely positioned proximate the natural lens surface 62, as described.

FIG. 16 is a perspective view showing the folded lens unit 10, held as in FIG. 8 by the blades or lens grasping arms 30 and 31 of the tool 70, as the lens-folding elements 24 and 25 are retracted endwise to free them from the folded lens unit. Arm extensions 30b and 31b are suitably manipulable to move the elements 30 and 31 toward and away from one another.

The lens insert 10 is characteristically very thin and highly light refractive.

FIGS. 1–15 and/or the specification disclose various aspects of a preferred form of the invention, other forms of the invention and aspects thereof being usable.

I claim:

1. The method of compacting an artificial lens for implantation into the eye, that includes
   a) imparting to the lens an M shape having two laterally spaced legs interconnected by a U-shaped portion, and
   b) laterally deflecting said legs toward and into compacting relation with said U-shaped portion,
   c) and including providing a lens inserter having two arms, and causing said arms to embrace said lens legs after compacting deflection of said legs as aforesaid.

2. The method of claim 1, wherein said imparting includes folding the lens at loci proximate the interconnection of said legs with said U-shaped portion, and also at a locus proximate a crest defined by said U-shaped portion.

3. The method of claim 2 that includes providing a bar, and folding the lens under said bar to produce said U-shaped portion.

4. The method of claim 3 including providing structure including two deflectors and displacing them adjacent said legs to deflect said legs as aforesaid.

5. The method of claim 1, wherein said deflecting of the legs includes displacing them toward a crest defined by said U-shaped portion.

6. The method of claim 1 wherein said U-shaped portion has two segments which are compacted toward one another in response to said deflecting.

7. The method of claim 1, which includes folding the lens to form three folds, and grasping the folded lens to hold it in folded state, and then inserting the folded lens into the eye through an opening formed in the eye.

8. The method of claim 1, wherein the lens consists of one of the following:
   i) collamer
   ii) silicone resin.

9. The method of claim 1, wherein said implanting positions the lens in the eye zone between the iris and the cornea of the eye, and including releasing the lens to allow the lens to unfold in said eye zone, the lens presented toward the natural lens of the eye.

10. The method of claim 9 including manipulating said lens to extend in the intraocular eye zone between the iris and the natural lens of the eye.

11. The method of claim 10 wherein said manipulating includes
   i) first deflecting a first edge portion of the lens into said eye zone between the iris and the natural lens, and
   ii) subsequently deflecting a second edge portion of the lens into said eye zone between the iris and the natural lens.

12. The method of claim 11 including allowing haptics defined by the lens to become anchored to eye tissue.

13. The method of compacting an artificial lens for implantation into the eye, that includes
   a) imparting to the lens an M shape having two laterally spaced legs interconnected by a U-shaped portion, and
   b) laterally deflecting said legs toward and into compacting relation with said U-shaped portion,
   c) said imparting including folding the lens at loci proximate the interconnection of said legs with said U-shaped portion, and also at a locus proximate a crest defined by said U-shaped portion,
   d) providing a bar, and folding the lens under said bar to produce said U-shaped portion,
   e) providing structure including two deflectors and displacing them adjacent said legs to deflect said legs as aforesaid,
   f) and including relatively withdrawing said bar away from the compacted lens, to allow the lens to be supported by said deflectors.

14. The method of compacting an artificial lens for implantation into the eye, that includes
   a) imparting to the lens an M shape having two laterally spaced legs interconnected by a U-shaped portion, and
   b) laterally deflecting said legs toward and into compacting relation with said U-shaped portion,
   c) said imparting including folding the lens at loci proximate the interconnection of said legs with said U-shaped portion, and also at a locus proximate a crest defined by said U-shaped portion,
   d) providing a bar, and folding the lens under said bar to produce said U-shaped portion,
   e) providing structure including two deflectors and displacing them adjacent said legs to deflect said legs as aforesaid,
   f) and including relatively slidably supporting said bar on said structure, to allow relative withdrawing of the bar away from said U-shaped lens portion, whereby the lens may be supported by said deflectors.

15. The method of compacting an artificial lens for implantation into the eye, that includes
   a) imparting to the lens an M shape having two laterally spaced legs interconnected by a U-shaped portion, and
   b) laterally deflecting said legs toward and into compacting relation with said U-shaped portion,
   c) said imparting including folding the lens at loci proximate the interconnection of said legs with said U-shaped portion, and also at a locus proximate a crest defined by said U-shaped portion,
   d) providing a bar, and folding the lens under said bar to produce said U-shaped portion,
   e) providing structure including two deflectors and displacing them adjacent said legs to deflect said legs as aforesaid,
   f) and including providing lens edge grabbers associated with said structure, and relatively displacing said grabbers to effect bowing of the lens under said bar.

16. Apparatus for folding a foldable plastic lens unit, for insertion, via a small wound, into the eye, including multiple lens fold forming elements to form at least three lens folds, one element comprising a bar, and wherein said elements include generally H-shaped bar structure.

17. The apparatus of claim 16 wherein said bar structure includes one bar removably carried by two other bars.

18. The apparatus of claim 16 including lens-edge grabbing structure carrying said bar.

19. The apparatus of claim 18 including lens edge camming structure carried by said grabbing structure.

20. The method of folding a plastic lens using lens edge lifters, that includes:

i) displacing said lifters toward lens edges to lift the lens, ii) and effecting folding of the lens at a zone above said lifters in response and as the lens is lifted iii) said folding creating an M-shaped lens folded at three locations, with legs compacted against opposite sides of a thereby created and compacted medial U-shaped portion, iv) and including providing a lens inserter having two arms, and causing said arms to embrace said lens legs after compacting deflection of said legs as aforesaid.

* * * * *